United States Patent
Bach et al.

(10) Patent No.: US 9,505,684 B2
(45) Date of Patent: Nov. 29, 2016

(54) METHOD AND SYSTEM FOR PRODUCING LOW-OXYGENATE OLEFIN FLOWS

(75) Inventors: Hermann Bach, Frankfurt (DE);
Thomas Renner, Frankfurt (DE);
Martin Rothaemel, Frankfurt (DE);
Michael Wilken, Frankfurt (DE)

(73) Assignee: AIR LIQUIDE GLOBAL E&C SOLUTIONS GERMANY GMBH, Frankfurt am Main (DE)

(*) Notice: Subject to any disclaimer, the term of this patent is extended or adjusted under 35 U.S.C. 154(b) by 875 days.

(21) Appl. No.: 13/697,825

(22) PCT Filed: Apr. 21, 2011

(86) PCT No.: PCT/EP2011/002038
§ 371 (c)(1),
(2), (4) Date: Nov. 14, 2012

(87) PCT Pub. No.: WO2011/144288
PCT Pub. Date: Nov. 24, 2011

(65) Prior Publication Data
US 2013/0060073 A1    Mar. 7, 2013

(30) Foreign Application Priority Data
May 20, 2010  (DE) .................. 10 2010 022 138

(51) Int. Cl.
*C07C 1/22* (2006.01)
*C07C 7/04* (2006.01)
*B01D 3/00* (2006.01)

(52) U.S. Cl.
CPC .. *C07C 7/04* (2013.01); *B01D 3/00* (2013.01)

(58) Field of Classification Search
CPC ...................................................... B01D 3/36
USPC ....... 585/833, 809, 804, 314, 315, 733, 802, 585/638, 639, 640; 203/29, 49, 39, 98
See application file for complete search history.

(56) References Cited

U.S. PATENT DOCUMENTS

| | | | |
|---|---|---|---|
| 5,609,734 A | 3/1997 | Streicher et al. | |
| 7,015,369 B2 | 3/2006 | Hack et al. | |
| 7,074,971 B2 | 7/2006 | Van Egmond et al. | |
| 7,678,958 B2 * | 3/2010 | Cheng et al. | 585/809 |
| 7,989,669 B2 * | 8/2011 | McGlamery, Jr. | C07C 1/20 585/518 |
| 8,058,498 B2 | 11/2011 | Jensen et al. | |
| 2004/0176646 A1 | 9/2004 | Van Egmond et al. | |
| 2005/0187358 A1 * | 8/2005 | Van Egmond | C08F 6/001 526/68 |
| 2008/0024908 A1 | 1/2008 | Nakamiya et al. | |
| 2008/0242908 A1 | 10/2008 | McGlamery et al. | |

FOREIGN PATENT DOCUMENTS

| | | |
|---|---|---|
| CN | 1358695 A | 7/2002 |
| CN | 1304342 C | 3/2005 |
| DE | 102004052658 B3 | 12/2005 |
| EP | 0448000 A1 | 9/1991 |
| EP | 0652194 A1 | 5/1995 |
| EP | 0882692 A1 | 12/1998 |
| EP | 0933345 A1 | 8/1999 |
| EP | 1289912 A1 | 3/2003 |
| WO | WO 03020672 A1 | 3/2003 |
| WO | WO 03020678 A2 | 3/2003 |
| WO | WO 03020671 A9 | 4/2004 |

OTHER PUBLICATIONS

European Patent Office, International Search Report in International Patent Application No. PCT/EP2011/002038 (Jul. 26, 2011).
Ullmann's Encyclopedia of Industrial Chemistry, Sixth Edition, 1998 Electronic Release, keyword "Polyolefins", chapter 2.3.1 "Propene".
"Separation Engineering", Junsheng Zhu, China University of Science and Technology Press, pp. 1-3, First Edition, Aug. 1992.

* cited by examiner

Primary Examiner — Sharon Pregler
(74) Attorney, Agent, or Firm — Leydig, Voit & Mayer, Ltd.

(57) ABSTRACT

A process and a plant for producing an olefin stream from a hydrocarbon mixture feed stream, wherein the olefin stream is depleted as regards its content of oxygen-containing organic compounds (oxygenates) as compared to the feed stream. The hydrocarbon mixture feed stream is charged to a separation column operated by a thermal separation process, for example to a distillation column, wherein a material stream enriched in oxygenates is withdrawn via a side outlet and removed from the process. The process according to the invention is particularly useful for processing the product streams obtained in the olefin synthesis by an OTO process.

20 Claims, No Drawings

METHOD AND SYSTEM FOR PRODUCING LOW-OXYGENATE OLEFIN FLOWS

CROSS REFERENCE TO RELATED APPLICATIONS

This application is a U.S. National Phase application under 35 U.S.C. §371 of International Application No. PCT/EP2011/002038, filed on Apr. 21, 2011, and claims benefit to German Patent Application No. DE 10 2010 022 138.4, filed on May 20, 2010. The International Application was published in German on Nov. 24, 2011, as WO 2011/144288 A1 under PCT Article 21(2).

FIELD

This application relates to a process for producing an olefin stream from a hydrocarbon mixture feed stream, wherein the olefin stream is depleted as regards its content of oxygen-containing organic compounds (oxygenates) as compared to the feed stream. In particular, this application relates to a process for producing and providing a propylene stream from a hydrocarbon feed stream, which is obtained as product stream in the olefin synthesis by reacting oxygenates such as alcohols and/or ethers on molecular sieve catalysts. This application also relates to a plant for carrying out the process according to an embodiment of the invention.

BACKGROUND

Hydrocarbon compounds are base materials of the chemical industry and starting materials for a multitude of secondary products. Typically, the hydrocarbon compounds are obtained in the primary production processes in the form of mixtures which by means of separation processes—above all the fractional distillation—must be separated into individual fractions or pure substances. The interconnection of the separators used in the conventional processes leads to large dimensions of the individual equipment parts and to a high specific consumption of operating materials.

Accordingly, the optimum design of the separation process is of high importance. The hydrocarbon compounds should be produced in rather pure form without the presence of oxygen-containing organic compounds (oxygenates). Oxygenates are understood to be compounds which exclusively are composed of carbon, hydrogen and oxygen; in general, these are alcohols or ethers, which can also be admixed to the gasoline.

In particular in the olefin synthesis by reaction of oxygenates such as methanol and/or dimethyl ether (DME) on molecular sieve catalysts, as it is described for example in the European Patent Applications EP 0448000 A1 and EP 0882692 A1 and the European Patent EP 1289912 B1, it is the object to remove small amounts of the oxygenates used as educt, such as methanol or dimethyl ether, from the reaction product, a hydrocarbon stream rich in olefins, in an efficient way, since the oxygenates are catalyst poisons in the succeeding further processing of the olefins to polyolefins. In Ullmann's Encyclopedia of Industrial Chemistry, Sixth Edition, 1998 Electronic Release, keyword "Polyolefins", chapter 2.3.1 "Propene", limit values are indicated for the content of oxygenate components in a propylene stream with polymerization purity (so-called "polymer grade propylene"). For example, the tolerable concentration of methanol in propylene with polymerization purity maximally amounts to 5 vol-ppm.

For separating smaller amounts or lower concentrations of oxygenates to achieve polymerization purity, adsorptive processes also are suitable. The same are also employed as downstream separation processes for example after a distillative separation of oxygenate, in order to definitely comply with the required limit values.

In the processes taught in the above-mentioned European patent applications and patents, the olefin synthesis is carried out in fixed-bed reactors with one or more catalyst beds. With increasing deactivation of the catalysts used, the oxygenate concentration in the olefin product stream also rises continuously, so that the separation process to be used must also be suitable for time-varying oxygenate concentrations in the feed stream to be treated.

According to the prior art, the oxygenates are separated from the hydrocarbon compounds by a classically connected distillation or a physical wash. In particular in large-scale industrial plants this is costly and expensive. The documents WO 03/020671, WO 03/020672 and WO 03/020678 describe processes for the extractive distillation of olefins.

The U.S. Pat. No. 7,678,958 B2 describes a process for removing DME from an olefin stream by means of distillation and a downstream water wash, which was obtained in the conversion of oxygenates to olefins (OTO). The process includes the distillation of the olefin stream, so that DME together with propane is obtained as bottom product and thus removed from the olefin stream. The olefin stream then can be supplied to one or more further distillation stages, in order to ultimately obtain an ethylene stream and a propylene stream with polymerization purity, wherein the DME concentration in both streams does not exceed 10 wt-ppm. The DME is removed from the propane stream by water washing, and the separated DME is recirculated to the OTO reactor.

The German Patent Specification DE 102004052658 B3 teaches a process for removing oxygenates from hydrocarbon mixtures, in which the remaining amount of oxygenates in the olefin stream is reduced to below 1 ppm, and a separation into partial fractions is achieved, wherein the apparatus dimensions and the specific consumptions of operating materials are minimized. The solution of this object is achieved in that the mixture of hydrocarbons and oxygenates is processed in a two-stage separation process. The feedstock hydrocarbon mixture is present in a two-phase form, wherein the heavier hydrocarbons are present in the liquid phase. The two phases are not charged together to one distillation column as conventionally, but are each guided separately into two distillation columns. From the liquid phase in the first column a light fraction is separated, in which the olefin product and oxygenates are contained. The gas phase is charged to the second column together with the light fraction of the first column. This second column is an extractive distillation column.

The mixture is separated into a light and a heavy hydrocarbon cut. In the process, a solvent is supplied into the upper part of the column, which dissolves the oxygenates. As a result, the content of oxygenates is distinctly decreased as compared to the prior art. Various components are taught as solvent, such as the alcohol methanol used as educt in the preceding methanol-to-propylene process (MTP® process). It is advantageous that thus a substance inherent to the process is used as solvent, which is available anyway, and the separated oxygenate can be recirculated to the olefin synthesis together with a residual content of methanol.

The distillative processes for oxygenate separation as taught in the prior art have in common that the oxygenate to be separated is obtained with a hydrocarbon fraction with similar boiling point, which subsequently must be separated from the hydrocarbon fraction by a further step, for example by an additional distillation step, an extractive distillation step, by washing or by adsorption or by a combination of several of these measures.

SUMMARY

Provided is process for producing a low-oxygenate olefin stream from a hydrocarbon mixture feed stream by a thermal separation process, the process comprising: (1) supplying a hydrocarbon mixture feed stream to a column operated by a thermal separation process, wherein the hydrocarbon mixture feed stream comprises a first olefin, a first paraffin of the same carbon number as the olefin, a second paraffin of a higher carbon number than the olefin, a second olefin of a higher carbon number than the first olefin, and an oxygenate; (2) withdrawing, in a lower region of the column, a bottom product stream, comprising a bottom product which is enriched in paraffins of the same, higher, or the same and higher carbon number than the first olefin, and in olefins of a higher carbon number than the first olefin; (3) withdrawing, in an upper region of the column, a low-oxygenate olefin stream, comprising a top product which is enriched in the first olefin and depleted of the oxygenate; (4) withdrawing, in a side draw, an oxygenate stream, which is enriched in the oxygenate; and (5) removing the oxygenate stream from the process.

DETAILED DESCRIPTION

An embodiment of the present invention provides an alternative process for the production of an olefin stream from a hydrocarbon mixture feed stream, wherein the olefin stream is depleted as regards its content of oxygenates as compared to the feed stream. A process according to the invention has technical simplicity, high energy efficiency and the lack in particular of auxiliary substances foreign to the process. In particular, an objective of the invention is to provide a process in which the oxygenates are obtained in a material stream which either can be used directly or whose further processing, for example by distillation or adsorption, requires less effort than in the processes known in the prior art.

A solution according to an embodiment of this invention substantially results from a process described above in the summary, in conjunction with the features of the generic part, in that in a process for the production of a low-oxygenate olefin stream from a hydrocarbon mixture feed stream, which comprises the olefin, paraffins of the same or a higher carbon number than the olefin, olefins of a higher carbon number and at least one oxygenate, a thermal separation process is used, wherein the hydrocarbon mixture feed stream is supplied to a column operated by the thermal separation process, wherein in the lower region of the column a bottom product stream enriched in the paraffins of the same and/or a higher carbon number and in the olefins of a higher carbon number is withdrawn, wherein in the upper region of the column a low-oxygenate olefin stream enriched in the olefin and depleted of the oxygenate is withdrawn as top product stream, and wherein in the side draw a stream enriched in oxygenate is withdrawn and removed from the process.

Further advantageous aspects of the invention can be taken from the sub-claims. In a particularly preferred aspect of the process according to the invention the oxygenate is a dialkyl ether which as regards its carbon number is reduced by one as compared to the olefin.

In the prior art distillative processes for separating oxygenates from hydrocarbon mixtures, which contain olefins and paraffins with similar boiling point and similar molar mass as the oxygenate, the prejudice among experts so far has been that the oxygenate always leaves the distillation with the bottom product. This is understandable with reference to the normal boiling points and molar masses for the $C_3$ and $C_4$ systems listed in the Table 1 by way of example. The distance of the normal boiling points between propane and DME is 18° C.; this is the largest boiling point distance of the compounds listed in the table and therefore is recommendable as starting point for the distillative separation of the hydrocarbon mixture, which then is separated according to the processes described in the prior art into a low-boiling top product, comprising propylene and propane, and a high-boiling bottom product, comprising DME and the isomeric butanes and butenes.

TABLE 1

| Component | Molar mass in g/mol | Normal boiling point in ° C.[1)] |
|---|---|---|
| Propylene | 42.08 | −47 |
| Propane | 44.10 | −42 |
| Dimethyl ether (DME) | 46.07 | −24 |
| i-Butane | 58.12 | −11 |
| 1-Butene | 56.11 | −6 |
| n-Butane | 58.12 | 0 |
| 2-Butene (E) | 56.11 | +1 |
| 2-Butene (Z) | 56.11 | +4 |

[1)]All data from NIST Chemistry WebBook, http://webbook.nist.gov/chemistry/, converted into ° C. The normal boiling point is the boiling point at 101.25 kPa.

In accordance with an embodiment of the present invention, it has now surprisingly been found that in a separation column operated by a thermal separation process a material stream can be obtained via a side draw, which is enriched in oxygenate both with respect to the top product and with respect to the bottom product. In this way, oxygenates can be removed from the separation process in an efficient way, so that a low-oxygenate olefin stream depleted of the oxygenate can be obtained as top product stream, which as regards its oxygenate concentration either already satisfies the requirements for the succeeding further use or further processing, or whose further purification can be carried out with less expenditure than in the processes known in the prior art. In the lower region of the separation column a bottom product stream enriched in the paraffins of the same and/or a higher carbon number and enriched in the olefins of a higher carbon number is withdrawn, which mostly still contains significant residual contents of oxygenate. In dependence on the intended further use or further processing, the same are however not disturbing. When the bottom product stream or parts thereof are recirculated to the olefin synthesis for example in the case of the OTO reaction, the residual content of oxygenates can additionally be converted to olefins when again passing through the synthesis reactor.

The formation of concentration maxima of components over the height of the separation column—the skilled person here speaks of concentration bellies—frequently renders the operation of the separation column susceptible to instabilities, which the skilled person usually eliminates by mounting a so-called side draw at the column. At the height of the separation column at which the respective component is present in maximum concentration, a side draw conduit operated continuously or at intervals is installed, with which the disturbing component then is selectively removed from the separation column. Depending on concentration and quantity, the concentration belly can be removed completely or at least be stabilized, so that a trouble-free operation of the separation column again becomes possible. In general, however, the skilled person will try to avoid the formation of concentration bellies by a suitable design of the separation process and the separation column. In the case of an embodiment of the present invention, the formation of such concentration belly is favorable for oxygenates, since the latter can be withdrawn at this point from the separation column in concentrated form. Furthermore, this results in the further advantage that not only the oxygenate can be withdrawn through a side draw and be removed from the process, but that in this way the concentration of the oxygenate in the upper part of the separation column also can be reduced as compared to an operation without side draw.

In a preferred aspect of the invention, the olefin is propylene and the oxygenate is dimethyl ether. The paraffins of the same and/or a higher carbon number withdrawn as bottom product stream in the lower region of the separation column comprise propane and the isomeric butanes as well as traces of paraffin hydrocarbons with more than four carbon atoms. The olefins of a higher carbon number likewise withdrawn with the bottom product stream comprise the isomeric butenes as well as traces of propylene and of olefin hydrocarbons with more than four carbon atoms. Accordingly, the hydrocarbon mixture feed stream contains propylene, propane, the isomeric butenes and butanes, dimethyl ether as well as higher ($C_{5+}$) paraffinic and olefinic hydrocarbons in trace amounts.

The separation of this hydrocarbon mixture feed stream is important in connection with the processing of the $C_3$ product stream from an olefin synthesis reaction. Lighter hydrocarbons ($C_2$ fraction) also can get into the separation column; the performance of a process according to embodiments of the invention however is not impaired thereby.

Particularly preferably, the separation of the oxygenate from the hydrocarbon mixture feed stream is effected by distillation or rectification. These separation methods are proven in the art, and for the solution of his specific separation problem the skilled person can choose from a wide variety of types of separation columns, for example with discrete separation trays in various embodiments, but also those with structured packings. When using, like in a method according to the invention, not the extractive distillation, but the classical distillation or rectification without additional extracting agent, the additional handling effort for the latter can also be omitted.

In a further, preferred aspect it is provided that the side draw for withdrawing the material stream enriched in oxygenate is arranged at least at one theoretical and/or real plate above the withdrawal point of the bottom product and at least at one theoretical and/or real plate below the withdrawal point of the top product. In this way, the oxygenate in the top product largely is depleted, and the oxygenate concentration in the bottom product is reduced significantly as compared to that in the side draw stream. Due to the higher requirements of the top product stream as regards the removal of oxygenates, it is recommendable to arrange the side draw in the lower region of the column, i.e. above the withdrawal point of the bottom product, but below the inlet point for the hydrocarbon mixture feed stream.

Preferably the hydrocarbon mixture feed stream is obtained as product stream of an olefin synthesis reaction in which, proceeding from alcohols and/or ethers, olefins are formed. As explained already in the prior art discussed above, different process variants of the conversion of oxygenates to olefins (OTO) have been described already and in part have already attained technical maturity, such as the Lurgi MTP® process. When processing the $C_3$ product from the OTO process, the task is to remove residual contents of the DME serving as feedstock of the olefin synthesis from the propylene product, in order to achieve the required degrees of purity of the propylene product, for example polymerization purity. A process according to the invention has proven particularly suitable for this purpose.

In a further aspect of the invention it is provided to recirculate the material stream enriched in oxygenates, which is obtained in the side draw of the separation column, into the olefin synthesis reaction. Due to the combination of a process according to the invention with the upstream olefin synthesis, for example by an OTO process, a particularly high efficiency thus is achieved, since the oxygenates withdrawn in the side draw are charged to the OTO reactor in concentrated form and thus can be converted to additional olefin in a particularly efficient way. Furthermore, a part of the bottom product obtained when employing a process according to the invention, which still contains significant amounts of oxygenates, paraffins with the same or a higher carbon number than the olefin, and olefins with a higher carbon number, can also be charged to the OTO reactor, since paraffins frequently are admixed to the reactor feedstock for OTO processes as an inert or diluent gas, in order to better control the heat tonality of the reactions occurring in the olefin synthesis. Again, a part of the oxygenates left in the bottom product as well as a part of the olefins of a higher carbon number is converted to additional olefin, preferably ethylene and/or propylene.

According to a particularly preferred embodiment of the invention, the top product stream of the separation column is supplied to at least one further processing step, preferably to a distillation or rectification or an adsorption stage. In this way, it is ensured that the high requirements as regards the polymerization purity are definitely complied with. An example for a further processing step of the low-oxygenate top product stream is the distillative removal of ethane, ethylene and lighter components, in order to obtain a stream which contains propane, propylene and small residual amounts of oxygenates and corresponds to a so-called chemical-grade propylene which can directly be used in various consecutive processes without further processing.

An embodiment of the invention also relates to a plant for producing a low-oxygenate olefin stream from a hydrocarbon mixture feed stream, comprising the olefin, paraffins of the same and a higher carbon number than the olefin, olefins of a higher carbon number and at least one oxygenate, by means of a thermal separation process. It is characterized by a separation column operated by the thermal separation process, an inlet conduit via which the hydrocarbon mixture feed stream is supplied to the separation column, a discharge conduit for the bottom product stream withdrawn in the lower region of the column, enriched in the paraffins of the same and/or a higher carbon number and in the olefins of a higher carbon number, a discharge conduit for the top product stream withdrawn in the upper region of the separation column, enriched in the olefin and depleted of the oxygenate, a side draw conduit for withdrawing a material stream enriched in oxygenate in the side draw, and means for heating the separation column.

In a particularly preferred aspect of the plant according to an embodiment of the invention it is provided that the side draw conduit is arranged at least at one theoretical and/or real plate above the withdrawal point of the bottom product and at least at one theoretical and/or real plate below the withdrawal point of the top product and below the inlet point for the hydrocarbon mixture feed stream. As already explained above, it thereby is ensured that the oxygenate in the top product largely is depleted.

Further developments, advantages and possible applications of embodiments of the invention can also be taken from the following description of exemplary embodiments and numerical examples. All features described form embodiments of the invention per se or in any combination, independent of their inclusion in the claims or their back-reference.

The following exemplary embodiments relate to the distillative processing of a product stream from the MTP® process, in which olefins, in particular propylene, are generated from methanol as feedstock via the intermediate product DME. The conditions and process parameters to be chosen when carrying out the MTP® process are known per se to the skilled person; they are also set forth in the documents EP 0448000 A1, EP 0882692 A1 and EP 1289912 B1 already discussed above, with the technical features disclosed therein being included in the disclosure of the present patent application by reference. They are part of the teaching of the process according to embodiments of the invention and of particular aspects thereof.

EXAMPLE 1 (INVENTIVE)

Experiments were carried out concerning the distillative separation of a hydrocarbon mixture feed stream, which originated from an upstream olefin synthesis operated by the MTP® process. The hydrocarbon stream to be separated contained ethylene, propylene, propane, butanes and butenes as well as higher hydrocarbons, but also significant amounts of DME. The separation column used for the distillative separation had a height of 4 m and was equipped with structured packings of the type Sulzer Mellapak®. Under the chosen process conditions, the separation column had a separation efficiency of 20 theoretical plates, the height of a theoretical plate (HETP value) thus was about 0.20 m. The separation column was operated under a pressure of 1.83 MPa(a). The temperature in the bottom of the separation column was 100 to 120° C., the temperature at the column head was about 40° C. The reflux ratio was 25. The feed line for the hydrocarbon mixture feed stream was located at a height of 2 m, calculated from the deepest point of the separation column, i.e. approximately at the level of the 10th theoretical plate, wherein plate 1 corresponds to the top of the column and plate 20 corresponds to the bottom of the column. The side draw conduit was arranged at the level of the 14th plate at a height of 1.20 m.

Since the hydrocarbon mixture feed stream originated from the MTP® synthesis reactor, its composition varied in dependence on the run time of the MTP® process due to the progressive deactivation of the catalyst used there. Therefore, the above-stated conditions in its distillative separation also were subject to temporal changes. In Table 2, the operating conditions of the separation column and the compositions of the material streams involved are listed for a run time of 815 h. The concentrations of the main components of the material streams were determined by means of capillary gas chromatography (GC) with thermal conductivity detector by using standard GC methods. The determination of the trace components, in particular of the DME concentration in the top product, however was effected by means of gas chromatography/mass spectrometry coupling (GC/MS), also according to standard methods. The positions of the inflow and of the side draw conduit as well as the column pressure were not varied during the test period. Samples of the distillation products were taken at two points in the separation column (plate no. 6 and plate no. 14=position of the side draw conduit) and of the top and bottom product. The samples taken confirmed the existence of a concentration belly for DME in the vicinity of the 14th plate of the separation column.

TABLE 2

| Plate No. | Height m | Position - | T ° C. | DME vol-% | Ethylene vol-% | Propane vol-% | Propylene | Butane + Butene vol-% |
|---|---|---|---|---|---|---|---|---|
| 10 | 2.0 | center, inlet | 60 | 6.30 | 18.50 | 0.86 | 29.38 | 24.32 |
| 1 | 4.0 | top | 39 | 0.03 | 36.29 | 1.70 | 57.02 | <0.01 |
| 6 | 2.8 | above | 41 | 2.67 | 15.18 | 3.86 | 76.74 | 0.02 |
| 14 | 1.2 | below, side draw | 77 | 34.86 | 0.06 | 4.06 | 55.82 | 5.00 |
| 20 | 0 | bottom | 114 | 10.49 | 0.14 | <0.01 | 0.38 | 47.05 |

It can clearly be seen that a material stream enriched in DME is withdrawn via the side draw, whereas the top product of the distillation almost completely consists of ethylene and propylene and only contains DME traces as well as small amounts of propane and traces of butanes and butenes. The bottom product also contains significant amounts of DME; the same do not disturb there, because the bottom product, as explained in the description, can at least partly be recirculated to the MTP® synthesis reactor.

COMPARATIVE EXAMPLE

Before carrying out the above-described distillation experiments according to an embodiment of the invention, experiments were carried out in the same separation column, with the operating conditions of the separation column and also the composition of the hydrocarbon mixture feed stream largely corresponding to the conditions described above. However, the separation column was not equipped with a side draw. Although most of the DME could be separated with the bottom product, concentrations of up to 0.2 vol-% DME still occurred in the propylene-containing top product, which could not be reduced further by modifying the operating conditions of the separation column.

EXAMPLE 2 (INVENTIVE)

Long-term experiments were carried out concerning the continuous olefin synthesis according to the MTP® process, and in turn a separation column operated according to Example 1 was provided downstream of the MTP® synthesis reactor. Due to the progressive aging or deactivation of the catalyst used in the synthesis reactor, DME no longer is converted completely; the DME concentration in the product stream of the synthesis reactor therefore rises continuously. According to an embodiment of the invention, the separation column was operated with side draw and for comparison without side draw for different test periods. In Table 3, the measured DME concentrations in the top product are represented in dependence on the operating period of the pilot plant and the operating condition of the side draw. For comparison, the DME concentration in the hydrocarbon mixture feed stream also is represented in dependence on the run time which corresponds to the DME concentration at the draw of the synthesis reactor.

TABLE 3

| Run time | h | 23 | 47 | 71 | 95 | 119 | 143 | 167 | 179 | 191 | 203 | 215 | 227 | 239 | 263 | 275 | 299 | 311 |
|---|---|---|---|---|---|---|---|---|---|---|---|---|---|---|---|---|---|---|
| DME in feed stream | Vol-% | 0.11 | 0.14 | 0.16 | 0.19 | 0.22 | 0.30 | 0.35 | 0.45 | 0.63 | 0.42 | 0.81 | 0.55 | 0.73 | 0.71 | 0.85 | 0.99 | 1.08 |
| DME in top product | Vol-% | 0.01− | 0.01 | 0.01 | 0.01 | 0.01 | 0.01 | 0.02 | 0.02 | 0.02 | 0.02 | 0.02 | 0.02 | 0.02 | 0.02 | 0.05 | 0.09 | 0.12 | 0.06 |
| Side draw active[#)] | +/− | − | − | − | − | − | − | − | − | − | − | − | − | − | − | − | − | − | + |
| Run time | h | 323 | 335 | 347 | 359 | 371 | 383 | 395 | 407 | 419 | 431 | 443 | 455 | 467 | 479 | 491 | 503 | |
| DME in feed stream | Vol-% | 1.46 | 1.35 | 1.79 | 1.60 | 1.89 | 1.80 | 1.71 | 1.95 | 2.19 | 2.29 | 2.40 | 2.27 | 2.73 | 3.02 | 3.08 | 3.66 | |
| DME in top product | Vol-% | 0.07 | 0.07 | 0.09 | 0.06 | 0.08 | 0.09 | 0.10 | 0.07 | 0.05 | 0.05 | 0.05 | 0.04 | 0.07 | 0.24 | 0.28 | 0.33 | |
| Side draw active[#)] | +/− | + | + | + | + | + | + | + | + | + | + | + | + | + | − | − | − | − | |

[#)] + active, − not active

It can be seen that in operation of the side draw at run times between 311 and 467 h the concentration of the DME in the top product decreases distinctly and can safely be maintained below a value of 0.1 vol-%, despite the continuously rising DME concentration at the draw of the synthesis reactor. After putting the side draw out of operation at run times greater than 467 h, the DME concentration in the top product quickly rises.

Since with the method according to an embodiment of the invention the DME concentration in the top product of the separation column can safely and constantly be maintained below a specified limit value, it is recommendable for a further decrease of the DME concentration to supply the top product stream to a further separation process, for example the adsorption, which works particularly well with a constant concentration of the component to be separated.

INDUSTRIAL APPLICABILITY

An embodiment of invention provides a process for producing an olefin stream from a hydrocarbon mixture feed stream, which as compared to the processes known from the prior art is characterized by its technical simplicity and by the absence of additional extracting agents, in particular those foreign to the process. The advantages of the processes known in the prior art as regards the use of proven distillation and rectification processes still exist. In the case of the combination of a process according to the invention with an upstream olefin synthesis, for example by an OTO process, additional advantages are obtained by the material use of the oxygenates left in the side draw product stream or in the bottom product stream when recirculating these streams to the olefin synthesis reactor.

While the invention has been illustrated and described in the foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the attached claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B, and C" should be interpreted as one or more of a group of elements consisting of A, B, and C, and should not be interpreted as requiring at least one of each of the listed elements A, B, and C, regardless of whether A, B and C are related as categories or otherwise.

The invention claimed is:

1. A process for producing a dimethyl ether-poor, propylene-containing stream from a hydrocarbon mixture feed stream by distillation or rectification, the process comprising:
   (1) supplying a hydrocarbon mixture feed stream, comprising ethylene, propylene, propane, butenes, butanes, and dimethyl ether, to a distillation or rectification column;
   (2) withdrawing, in a lower region of the column, a bottom product stream, enriched in butanes and butenes;
   (3) withdrawing, in an upper region of the column, a top product stream, enriched in propylene and depleted of dimethyl ether;
   (4) withdrawing, in a side draw from the column, an oxygenate stream, which is enriched in dimethyl ether relative to propane, wherein a concentration ratio of the dimethyl ether to the propane is higher at the side draw than at an inlet position of the column; and
   (5) removing the oxygenate stream, withdrawn from the side draw, from the process.

2. The process of claim 1, further comprising performing a distillation process on the hydrocarbon mixture feed stream in the column.

3. The process of claim 1, wherein the side draw is arranged at least at one theoretical, real, or theoretical and real plate above the withdrawal point of the bottom product stream, and wherein the side draw is arranged at least at one theoretical, real, or theoretical and real plate below a withdrawal point of the top product stream.

4. The process of claim 1, wherein the hydrocarbon mixture feed stream is obtained as product stream of an olefin synthesis reaction in which, proceeding from a starting mixture comprising an alcohol, an ether, or a mixture thereof, one or more olefins are formed.

5. The process of claim 1, further comprising:
recycling the oxygenate stream to an olefin synthesis reaction.

6. The process of claim 1, further comprising:
supplying the top product stream to further processing, by which a concentration of the dimethyl ether in the top product stream is further reduced.

7. The process of claim 1, comprising the rectification.

8. The process of claim 4, wherein the starting mixture comprises an alcohol.

9. The process of claim 4, wherein the starting mixture comprises an ether.

10. The process of claim 4, wherein the starting mixture comprises an alcohol and an ether.

11. The process of claim 6, wherein the further processing comprises a distillation.

12. The process of claim 6, wherein the further processing comprises a rectification.

13. The process of claim 6, wherein the further processing comprises an adsorption.

14. The process of claim 1, wherein a dimethyl ether concentration in the side draw is greater than a propane concentration in the side draw.

15. The process of claim 1, wherein a dimethyl ether concentration in the side draw is more than 8-told greater than a propane concentration in the side draw.

16. The process of claim 1, wherein the top product comprises traces of $C_4$ hydrocarbons.

17. The process of claim 1, wherein the distillation or rectification column is operated at its base at 100 to 120° C.

18. The process of claim 1, wherein side draw comprises a $C_4$ component.

19. The process of claim 1, wherein a dimethyl ether concentration in the top product is maintained below 0.1 vol. % until aging or deactivation of catalyst in a synthesis reactor supplying the hydrocarbon mixture feed stream the dimethyl ether concentration in the top product.

20. The process of claim 1, wherein the side draw operates discontinuously.

* * * * *